US012600948B2

(12) United States Patent (10) Patent No.: US 12,600,948 B2
Eto et al. (45) Date of Patent: Apr. 14, 2026

(54) METHOD AND APPARATUS FOR PRODUCING PLATELET AND METHOD FOR DETERMINING OPERATING CONDITION OF APPARATUS FOR PRODUCING PLATELET

(71) Applicants: KYOTO UNIVERSITY, Kyoto (JP); MEGAKARYON CORPORATION, Kyoto (JP); SATAKE MultiMix Corporation, Toda (JP)

(72) Inventors: Koji Eto, Kyoto (JP); Sou Nakamura, Kyoto (JP); Yukitaka Ito, Kyoto (JP); Tomohiro Shigemori, Kyoto (JP); Yoshikazu Kato, Toda (JP)

(73) Assignees: KYOTO UNIVERSITY, Kyoto (JP); MEGAKARYON CORPORATION, Kyoto (JP); SATAKE MultiMix Corporation, Toda (JP)

( * ) Notice: Subject to any disclaimer, the term of this patent is extended or adjusted under 35 U.S.C. 154(b) by 691 days.

(21) Appl. No.: 16/628,451

(22) PCT Filed: Jul. 5, 2018

(86) PCT No.: PCT/JP2018/025537
§ 371 (c)(1),
(2) Date: Mar. 16, 2020

(87) PCT Pub. No.: WO2019/009364
PCT Pub. Date: Jan. 10, 2019

(65) Prior Publication Data
US 2021/0130781 A1 May 6, 2021

(30) Foreign Application Priority Data
Jul. 7, 2017 (JP) ................................. 2017-133592

(51) Int. Cl.
*C12N 5/078* (2010.01)
*B01F 27/90* (2022.01)
(Continued)

(52) U.S. Cl.
CPC ............ *C12N 5/0644* (2013.01); *B01F 27/90* (2022.01); *C12M 21/00* (2013.01); *C12N 2501/21* (2013.01)

(58) Field of Classification Search
CPC ...... A61K 35/19; A61K 35/545; A61K 35/14; C12M 1/02; C12M 3/08; C12M 21/00;
(Continued)

(56) References Cited

U.S. PATENT DOCUMENTS

2006/0216818 A1 9/2006 Amano
2014/0127815 A1 5/2014 Eto et al.
(Continued)

FOREIGN PATENT DOCUMENTS

CA 3003679 A1 5/2017
JP 61-149080 A 7/1986
(Continued)

OTHER PUBLICATIONS

Ishikawa, JP 2006/043668 A, EPO machine translation (Year: 2006).*
(Continued)

*Primary Examiner* — Kara D Johnson
(74) *Attorney, Agent, or Firm* — Myers Bigel, P.A.

(57) ABSTRACT

Methods of production and apparatuses for production for stably producing healthy and functional platelets, and methods for determining operating conditions of an apparatus for producing platelets are provided. The present invention relates to methods of production comprising a step of culturing megakaryocytes in a platelet production medium C, wherein the step of culturing comprises a step of stirring
(Continued)

a medium C in containers 1, 4 using stirring mechanisms 2, 5. In one method of production, the step of stirring comprises reciprocating stirring blades 21, 24 in the stirring mechanisms 2, 24 such that any of predetermined turbulent energy, shearing stresses, or Kolmogorov scale is produced, in the medium C. In another method of production, the step of stirring comprises pivoting a stirring blade 51 in the stirring mechanism 5 wherein a plurality of stationary members 53 is placed therearound in a bottom region 4e of the container 4 such that the step of stirring produces turbulence in the medium C. The present invention also relates to apparatuses for production for carrying out the method of production. The present invention also relates to a method for determining operating conditions of an apparatus for producing platelets.

5 Claims, 7 Drawing Sheets

(51) Int. Cl.

| | |
|---|---|
| *C12M 1/00* | (2006.01) |
| *A61K 35/12* | (2015.01) |
| *B01F 27/80* | (2022.01) |
| *B01F 31/00* | (2022.01) |
| *C12M 1/02* | (2006.01) |
| *C12M 3/00* | (2006.01) |

(58) Field of Classification Search
CPC ...... C12M 27/00; C12M 29/00; C12M 41/48; C12M 3/00; C12M 27/02; C12N 5/10; C12N 5/16; C12N 15/85; C12N 15/09; C12N 2015/8572; C12N 2500/25; C12N 2500/38; C12N 2501/125; C12N 2501/145; C12N 2501/165; C12N 2501/727; C12N 2501/734; C12N 2506/45; C12N 2510/04; C12N 2527/00; C12N 5/0644; B01F 27/112; B01F 27/91
See application file for complete search history.

(56) References Cited

U.S. PATENT DOCUMENTS

| | | | |
|---|---|---|---|
| 2015/0252315 A1 | 9/2015 | Wada et al. | |
| 2018/0318352 A1* | 11/2018 | Shigemori | ............. C12M 41/48 |
| 2020/0216807 A1 | 7/2020 | Eto et al. | |

FOREIGN PATENT DOCUMENTS

| | | | | |
|---|---|---|---|---|
| JP | 2006043668 | A | * | 2/2006 |
| JP | 2006-296423 | A | | 11/2006 |
| JP | 2016-21908 | A | | 2/2016 |
| JP | 2016021908 | | * | 2/2016 |
| JP | 2016021908 | A | * | 2/2016 |
| WO | 2012/157586 | A1 | | 11/2012 |
| WO | 2013/187359 | A1 | | 12/2013 |
| WO | WO-2017077964 | A1 | * | 5/2017 ............. A61K 35/19 |
| WO | 2018164040 | A1 | | 9/2018 |

OTHER PUBLICATIONS

Koichi et al. A reciprocating agitation culture apparatus having a medium extraction function (2016), JP2016021908, English translation, WIPO machine translation. (Year: 2016).*

Lounes et al. Description and evaluation of reciprocating plate bioreactors (1995), Bioprocess Engineering, 13, pp. 1-11. (Year: 2016).*

Nakamura et al. Expandable Megakaryocyte Cell Line Enable Clinically Applicable Generation of Platelets from Human Induced Pluripotent Stem Cells (2014), Cell Stem Cell, 14, pp. 535-548. (Year: 2014).*

Nakagawa et al. Two differential flows in a bioreactor promoted platelet generation from human pluripotent stem cell-derived megakaryocytes (2013) Experimental Hematology, 41, pp. 742-748 (Year: 2013).*

Kato et al. Reciprocating agitation and culture apparatus having culture medium extracting function (2016)vJP2016021908, WIPO English Translation. (Year: 2016).*

Lounes et al. Description and evaluation of reciprocating plate bioreactors (1995), Bioprocess Engineering, 13, pp. 1-11. (Year: 1995).*

Ahamed et al. In Vitro and In Vivo Evidence that Thrombospondin-1 (TSP-1) Contributes to Stirring- and Shear-Dependent Activation of Platelet-Derived TGF-b1 (2009), 4, pp. 1-10. (Year: 2009).*

Brogren et al. Platelets Retain High Levels of Active Plasminogen Activator Inhibitor 1 (2011), Plos One, 6, pp. 1-7 (Year: 2011).*

Machlus et al. CCL5 derived from platelets increases megakaryocyte proplatelet formation (2016) Blood, 127, pp. 921-926 (Year: 2016).*

International Search Report and Written Opinion of the International Searching Authority, International Application No. PCT/JP2018/025537, Oct. 2, 2018, 12 pp.

Machlus et al., "CCL5 derived from platelets increases megakaryocyte proplatelet formation", Blood, vol. 127, No. 7, Feb. 2016, pp. 921-926.

Junt et al., "Dynamic Visualization of Thrombopoiesis Within Bone Marrow", Science, vol. 317, Sep. 21, 2007, pp. 1767-1770.

"Notice of Reasons for Refusal and English language translation", JP Application No. 2019-527964, Apr. 15, 2022, 8 pp.

Nakagawa, Yosuke , et al., "Two differential flows in a bioreactor promoted platelet generation from human pluripotent stem cell-derived megakaryocytes", Experimental Hematology, vol. 41, No. 8, Aug. 2013, pp. 742-748.

"Communication with Supplementary European Search Report", EP Application No. 18828313.9, Feb. 17, 2021, 9 pp.

Dunois-Larde, Claire , et al., "Exposure of human megakaryocytes to high shear rates accelerates platelet production", Blood, vol. 114, No. 9, Aug. 27, 2009, pp. 1875-1883.

Ito, Yukitaka , et al., "Turbulence Activates Platelet Biogenesis to Enable Clinical Scale Ex Vivo Production", Cell, vol. 173, No. 3, Jul. 26, 2018, pp. 636-648.

Schlinker, Alaina C., et al., "Separation of In-Vitro-Derived Megakaryocytes and Platelets Using Spinning-Membrane Filtration", Biotechnol .Bioeng., vol. 112, No. 4, Nov. 19, 2014, pp. 788-800.

* cited by examiner (A)

(B)

(C)

(A)

(B)

METHOD AND APPARATUS FOR PRODUCING PLATELET AND METHOD FOR DETERMINING OPERATING CONDITION OF APPARATUS FOR PRODUCING PLATELET

RELATED APPLICATIONS

This application is a 35 U.S.C. § 371 national stage application of PCT Application No. PCT/JP2018/025537, filed on Jul. 5, 2018, which claims priority from Japanese Patent Application No. 2017-133592, filed on Jul. 7, 2017, the contents of which are incorporated herein by reference in their entireties. The above-referenced PCT International Application was published in the Japanese language as International Publication No. WO 2019/009364 A1 on Jan. 10, 2019.

TECHNICAL FIELD

The present invention relates to methods and apparatuses for producing platelets. The present invention further relates to methods for determining operating conditions of an apparatus for producing platelets.

BACKGROUND ART

Platelet formulations are administered to patients having major bleeding in a surgical operation or an injury or bleeding tendency associated with thrombocytopenia after treatment with an anticancer agent for the purpose of treatment and prevention of symptoms thereof. The production of the platelet formulations currently depends on blood donation, but a stable supply of platelets, which is safer in view of infections is demanded. In order to meet the need, methods for producing platelets from megakaryocytes cultured in vitro have been developed up until now. The present applicants have been developing methods for establishing immortalized megakaryocyte progenitor cell lines (im-MKCLs), which are immortalized cells generated from pluripotent stem cells as a source (see, for example, Patent Document 1). Moreover, the present applicants have studied methods for producing platelets using these immortalized megakaryocyte progenitor cell lines and also apparatuses used in such production (see, for example, Patent Document 2).

A wide range of research has been made on the mechanism by which platelets are produced from megakaryocytes. In such researches, it has been suggested that shedding of platelets is promoted by shearing forces depending on flow (see, for example, Non-Patent Document 1). Moreover, it has been reported that the chemokine CCL5 promotes platelet production from megakaryocytes (see, for example, Non-Patent Document 2).

CITATION LIST

Patent Document

[Patent Document 1]
International Publication No. WO 2012/157586
[Patent Document 2]
International Publication No. WO 2017/077964

Non Patent Document

[Non Patent Document 1]
Science 317 (5845), 1767-1770

[Non Patent Document 2]
Blood, 2016; 127(7):921-926

SUMMARY OF INVENTION

Technical Problem

Immortalized megakaryocyte progenitor cell lines have many advantages in that they can be preserved by freezing, that the promotion of artificial multinucleation is possible, and the like. More efficient methods and apparatuses for stably and massively producing platelets from these immortalized megakaryocyte progenitor cell lines according to the demand are desired.

Solution to Problem

To approach to the mass production of platelets, it is necessary to consider both of the steps megakaryopoiesis and platelet shedding. The approaches to megakaryopoiesis include increasing the number of cells serving as a source, and examples thereof include a method for producing immortalized megakaryocytes (Patent Literature 1) by the present inventors. Meanwhile, it has been suggested that platelet shedding is promoted by shearing forces (Non-Patent Literature 1). Moreover, it has been found that mechanisms for in vivo production of platelets include acute production of platelets induced by IL-1 alpha and steady production of platelets. The acute platelet production is characterized in that large amounts of platelets are produced in a short time, but the platelets produced have high Annexin V-positive rates and cannot circulate for a long time in the living body. Thus, platelets produced by such a mechanism are not suitable for use in a blood product. The present inventors focused their attention on the mechanism of platelet production in a steady state and identified the presence of factors that promote platelet production and found that it is possible to promote the release of platelet production promoting factors by adding turbulent energy or shearing stresses in certain ranges, using certain apparatuses, to a medium in which megakaryocytes at a mature stage are contained to increase the amount of produced healthy platelets suitable for blood products for transfusion, thereby completing the present invention.

Accordingly, the present invention provides items as follows.

[1] A method for producing platelets, comprising a step of culturing megakaryocytes in a platelet production medium, wherein the step of culturing comprises a step of stirring the platelet production medium in a container using a stirring blade and the step of stirring comprises reciprocating the stirring blade such that one or more indicators selected from the following are satisfied:

(a) turbulent energy of about 0.0005 $m^2/s^2$ to about 0.02 $m^2/s^2$;

(b) shearing stresses of about 0.2 Pa to about 6.0 Pa; and (c) a Kolmogorov scale of about 100 μm to about 600 μm.

[2] A method for producing platelets, comprising a step of culturing megakaryocytes in a platelet production medium, wherein the step of culturing comprises the step of stirring the platelet production medium in a container using a stirring blade pivotable around a vertical axis and having at least part of the stirring blade in a bottom region of the container, and the step of stirring comprises pivoting the stirring blade, wherein a plurality of stationary members is placed around the stirring blade in the bottom region, such that turbulence in the medium is caused by the pivoting of the stirring blade, in the medium.

[3] The method according to [1] or [2], comprising, prior to the step of culturing the megakaryocytes, a step of forcibly expressing an oncogene, a polycomb gene, and an apoptosis repressor gene in cells less differentiated than megakaryocytes to obtain immortalized mega-karyocytes.

[4] The method according to any one of [1] to [3], comprising a step of collecting platelets obtained in the step of culturing megakaryocytes.

[5] An apparatus for producing platelets, comprising:
a container that holds a medium in which megakaryo-cytes are contained; and
a stirring blade that reciprocates in the container,
wherein the apparatus for producing platelets produces platelets from megakaryocytes while the medium is stirred by reciprocating the stirring blade such that one or more indicators selected from the following are satisfied in the medium:
(a) turbulent energy of about 0.0005 $m^2/s^2$ to about 0.02 $m^2/s^2$;
(b) shearing stresses of about 0.2 Pa to about 6.0 Pa; and
(c) a Kolmogorov scale of about 100 μm to about 600 μm.

[6] An apparatus for producing platelets, comprising:
a container that holds a platelet production medium in which megakaryocytes are contained; and
a stirring mechanism that stirs the medium to produce turbulence in the medium,
wherein the stirring mechanism has a stirring blade pivotable around a vertical axis and having at least part of the stirring blade in a bottom region of the container and a plurality of stationary members placed around the stirring blade in the bottom region in the medium such that the turbulence is caused by the pivot of the stirring blade and
the apparatus produces platelets from the megakaryo-cytes while the medium is stirred by pivoting the stirring blade in the medium.

[7] A method for determining operating conditions of an apparatus for producing platelets comprising a recip-rocatable or pivotable stirring blade, the method com-prising the steps of:
calculating a correlation between one or more indica-tors selected from turbulent energy, shearing stresses, and a Kolmogorov scale and the number of platelets produced in the apparatus for production; and
determining operating conditions that provide the indi-cators with which the number of platelets produced becomes in a predetermined range.

[8] The method according to [7], wherein the operating conditions comprise having an average speed of recip-rocation of the reciprocatable stirring blade in the range of 50 mm/s to 500 mm/s.

[9] The method according to any one of [1] to [4], wherein the step of stirring comprises a step of adding platelet production promoting factors including MIF, NRDc, and IGFBP2 exogenously.

[10] The method according to [9], wherein the exog-enously added platelet production promoting factors further comprise TSP-1, PAI-1, and CCL5.

Advantageous Effects of Invention

By employing the methods and apparatuses according to the present invention, it is possible to promote the produc-tion of platelets from megakaryocytes and increase the amount of platelets produced. In addition, the platelets produced by the methods and apparatuses according to the present invention have low Annexin V levels and properties suitable to be used as blood products and are very useful in the production of blood products. Furthermore, the methods according to the present invention provide a guide to oper-ating conditions of a step of culturing megakaryocytes, in particular conditions of stirring. Accordingly, by providing unsteady stirring of a medium according to this guide, it is possible to determine operating conditions, suitable for the platelet production, of apparatuses even at different scales and/or of different types for megakaryocytes before the shedding of platelets to enable stable production of platelets.

BRIEF DESCRIPTION OF DRAWINGS

FIG. 10(A) illustrates the pro-portion of normal platelets that are CD41a-positive and CD42b-positive, FIG. 10(B) illustrates the proportion of P-selectin-positive platelets when platelets are not stimu-lated, and FIG. 10(C) illustrates the proportion of P-selectin-positive platelets when platelets are stimulated with ADP+ TRAP6.

FIG. 11(A) illustrates the pro-portion of annexin V-positive platelets when platelets are not stimulated and FIG. 11(B) illustrates the proportion of annexin V-positive platelets when platelets are stimulated with Ionomycin.

DETAILED DESCRIPTION OF THE INVENTION

Figure 1:
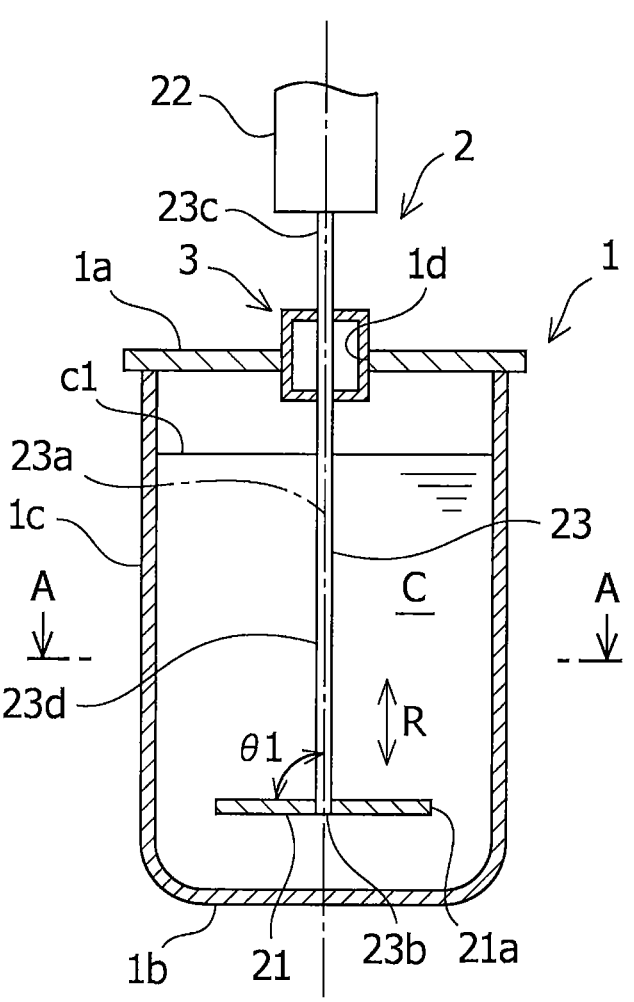
FIG. 1 is a longitudinal sectional view schematically illustrating an apparatus for producing platelets according to the first aspect of one embodiment of the present invention.

The present invention will be described in detail with reference to the embodiments. However, the present invention is not limited to the following embodiment.

[Methods of Production and Apparatuses of Production of Platelets]

According to the first aspect of one embodiment, the present invention relates to methods for producing platelets, and more particularly, to a method for producing platelets, comprising a step of culturing megakaryocytes in a platelet production medium, wherein the step of culturing comprises a step of stirring the platelet production medium in a container using a stirring blade and the step of stirring comprises reciprocating the stirring blade such that at least one indicator selected from the following are satisfied:

(a) turbulent energy of about 0.0005 $m^2/s^2$ to about 0.02 $m^2/s^2$;

(b) shearing stresses of about 0.2 Pa to about 6.0 Pa; and (c) a Kolmogorov scale of about 100 μm to about 600 μm. Moreover, according to the first aspect of one embodiment, the present invention relates to apparatuses for producing platelets for conducting the method of production.

According to the second aspect of one embodiment, the present invention relates to a method for producing platelets, and more particularly, to a method for producing platelets, comprising a step of culturing megakaryocytes in a platelet production medium, wherein the step of culturing comprises the step of stirring the platelet production medium in a container using a stirring blade pivotable around an approximately vertical axis and having at least part of the stirring blade in a bottom region of the container, and the step of stirring comprises pivoting the stirring blade, wherein a plurality of stationary members is placed around the stirring blade in the bottom region, such that turbulence in the medium is caused by the pivoting of the stirring blade, in the medium. Moreover, according to the second aspect of one embodiment, the present invention relates to apparatuses for producing platelets for conducting the method of production.

In the method for producing platelets according to the present invention, the megakaryocytes to be cultured in the step of culturing refers to megakaryocytes as defined below. The "megakaryocytes" are the largest cells present in the bone marrow in the living body and are characterized by releasing platelets. Moreover, the megakaryocytes are characterized by being positive for the cell surface markers CD41a, CD42a, and CD42b, and may further express a marker selected from the group consisting of CD9, CD61, CD62p, CD42c, CD42d, CD49f, CD51, CD110, CD123, CD131, and CD203c in addition. Although the "megakaryocytes" when multinucleated (polyploidized), have genomes that are as 16 to 32 times large as those of usual cells, the term "megakaryocytes", as used herein simply, refers to cells including both multinucleated megakaryocytes and megakaryocytes before multinucleation, as long as they have the characteristics described above. The term "megakaryocytes before multinucleation" is synonymous with "immature megakaryocytes" or "proliferative phase megakaryocytes". The megakaryocytes are not particularly limited, and they can be obtained by a variety of known methods and may be megakaryocytes obtained from any origin by any method.

The method for producing platelets according to the present invention preferably comprises, prior to the step of culturing, a step of forcibly expressing an oncogene, a polycomb gene, and an apoptosis repressor gene in cells less differentiated than megakaryocytes to obtain immortalized megakaryocytes.

Nonlimiting examples of the method for producing immortalized megakaryocytes include the method described in International Publication No. WO 2011/034073. In the method, immortalized megakaryocytes cell lines that proliferate without limit can be obtained by forcibly expressing an oncogene and a polycomb gene in the "cells less differentiated than megakaryocytes". Moreover, immortalized megakaryocytes cell lines can be obtained by forcibly expressing an apoptosis repressor gene in "cells less differentiated than megakaryocytes" according to the method described in International Publication No. WO 2012/157586. These immortalized megakaryocyte cell lines multinucleate and start releasing platelets by stopping forced expression of the genes. Accordingly, the step of culturing according to the present invention can be considered as a step of culturing with the forced expression of the genes stopped.

The step of obtaining immortalized megakaryocytes that can be conducted before the step of culturing may be combined with the method described in the above document to obtain megakaryocytes. In this case, the forced expression of an oncogene, a polycomb gene, and an apoptosis repressor gene may be simultaneous or sequential. The multinucleated megakaryocytes may be obtained, for example, by forcibly expressing an oncogene and a polycomb gene and suppressing the forced expression, and then forcibly expressing an apoptosis repressor gene and suppressing the forced expression. Moreover, the multinucleated megakaryocytes can be obtained by forcibly expressing an oncogene and a polycomb gene and an apoptosis repressor gene simultaneously and suppressing the forced expression simultaneously. The multinucleated megakaryocytes can be obtained by forcibly expressing an oncogene and a polycomb gene first and forcibly expressing an apoptosis repressor gene subsequently, and suppressing the forced expression simultaneously. As used herein, the step of forcibly expressing the genes may be referred to as the proliferative phase or the state of being capable of proliferating and the step of suppressing forced expression may be referred to as the maturation phase.

In the present invention, the "cells less differentiated than megakaryocytes" mean cells having the differentiation potency into megakaryocytes on a range of differentiation stages from hematopoietic stem cells to megakaryocytes. Nonlimiting examples of the cells less differentiated than megakaryocytes include hematopoietic stem cell lines, hematopoietic progenitor cells, CD34-positive cells, and megakaryocyte-erythroid progenitor (MEP) cells. These cells can be obtained, for example, by isolation from bone marrow, umbilical cord blood, or peripheral blood or by inducing differentiation from pluripotent stem cells such as ES cells and iPS cells, which are even more undifferentiated cells.

In the present invention, the "oncogene" refers to a gene that induces the oncogenic transformation of cells in the body and examples thereof include MYC family genes (for example, c-MYC, N-MYC, L-MYC), SRC family genes, RAS family genes, RAF family genes, and protein kinase family genes such as c-Kit, PDGFR, and Abl.

The "polycomb gene" is known as a gene that negatively controls the CDKN2a (INK4a/ARF) gene and functions to avoid cellular senescence (Ogura et al, Regenerative Medicine, vol. 6, No. 4, pp. 26-32; Jseus et al., Nature Reviews Molecular Cell Biology vol. 7, pp. 667-677, 2006; Proc. Natl. Acad. Sci. USA, vol. 100, pp. 211-216, 2003). Non-limiting examples of the polycomb gene include BMI1, Mel18, Ring1a/b, Phc1/2/3, Cbx2/4/6/7/8, Ezh2, Eed, Suz12, HDAC, Dnmt1/3a/3b.

The "apoptosis repressor gene" refers to a gene having the function of suppressing the apoptosis of cells and examples thereof include the BCL2 gene, the BCL-xL gene, the Survivin gene, and the MCL1 gene.

The forced expression of genes and the stop of the forced expression can be performed by a method described in International Publication No. WO 2011/034073, International Publication No. WO 2012/157586, International Publication No. WO 2014/123242, or Nakamura S et al., Cell Stem Cell. 14, 535-548, 2014, or another known method, or a method equivalent thereto. When a drug-responsive system of inducing gene expression such as the Tet-on (R) or Tet-off (R) system is used for the forced expression of genes and the removal thereof, for example, the corresponding drug, for example, tetracycline or doxycycline, may be included in the medium in the step of forced expression and removed from the medium to suppress the forced expression.

The conditions of culturing megakaryocytes for the forced expression of genes and the suppression (removal) of the forced expression may be usual conditions. For example, the conditions may include a temperature of about 35° C. to about 42° C., about 36° C. to about 40° C., or about 37° C. to about 39° C., and 5 to 15% $CO_2$, and/or 20% $O_2$.

Specifically, the step of forcibly expressing the genes in cells less differentiated than megakaryocytes can be conducted according to a method that is routine to those skilled in the art, for example, by introducing a vector expressing these genes or proteins or RNAs encoded by these genes into cells less differentiated than megakaryocytes. Furthermore, the step can be conducted by contacting a low molecular weight compound that induces the expression of these genes with cells less differentiated than megakaryocytes.

Vectors that may be used as the vector that expresses these genes are, for example, viral vectors such as retrovirus, lentiviral adenovirus, adeno-associated virus, herpesvirus, and Sendai virus, and animal cell expression plasmids (for example, pA1-11, pXT1, pRc/CMV, pRc/RSV, pcDNAI/Neo). The retroviral vector or the lentiviral vector is preferable in that they can be introduced at one single time. Examples of the promoter used in the expression vector include an EF-α promoter, a CAG promoter, an SRα promoter, an SV40 promoter, an LTR promoter, a CMV (cytomegalovirus) promoter, an RSV (Rous sarcoma virus) promoter, an MoMuLV (Moloney murine leukemia virus) LTR, and an HSV-TK (herpes simplex virus thymidine kinase) promoter. The expression vector may contain an enhancer, a poly A addition signal, a selection marker gene, an SV40 replication origin, and/or the like, as needed, besides the promoter. Examples of a useful selection marker gene include a dihydrofolate reductase gene, a neomycin resistance gene, a puromycin resistance gene and the like.

The expression vector according to the present invention may be a drug-responsive vector having a tetracycline-responsive element in the promoter region to control the expression of the genes by tetracycline or doxycycline. In addition, an expression vector having loxP sequences and a gene or a promoter region or both flanked by the loxP sequences may be used to cut out the gene from the vector using a Cre-loxP system.

The production of megakaryocytes may comprise at least one of: (a) a step of treating with an inhibitor of actomyosin complex function, cultured cells in which an apoptosis repressor gene is forcibly expressed; (b) a step of treating the cells with a ROCK inhibitor. These treatments allow more stable proliferation and multinucleation.

The optimal concentration and the like of the inhibitor of actomyosin complex function, the ROCK inhibitor, or the like in the treatment of cells can be determined beforehand by preliminary experiment by one skilled in the art. Moreover, the period and the method of the treatment and the like can be selected by one skilled in the art as appropriate. For example, in the treatment with the myosin heavy chain II ATPase inhibitor Blebbistatin, about 2 to 15 μg/ml or 5 to 10 μg/ml is added to the culture medium and, for example, a culture period of about 5 to 10 days and, in particular, for about 6 to 7 days is preferred. Moreover, the ROCK inhibitor Y27632 may be used at 5 to 15 μM, 8 to 12 μM, or preferably about 10 μM. The duration of treatment with Y27632 is 10 to 21 days, or preferably about 14 days.

Examples of the ROCK (Rho-associated coiled-coil forming kinase/Rho binding kinase) inhibitor include [(R)-(+)-trans-N-(4-pyridyl)-4-(1-aminoethyl)-cyclohexanecarboxamide, 2HCl·$H_2O$] (Y27632), and the like. Optionally, an antibody or a nucleic acid (for example, shRNA) that inhibits the Rho kinase activity may also be used as a ROCK inhibitor.

After the step of forced expression, a step of culturing in a platelet production medium megakaryocytes or megakaryocyte progenitor cells obtained in the step of forced expression. In the step of culturing, the suppression or stopping of the forced expression may be achieved, for example, by keeping the cells out of contact with the corresponding drug when a drug-responsive vector is used for the forced expression in the previous step. Specifically, when the forced expression of the genes is caused with doxycycline or tetracycline, the forced expression can be suppressed by culturing the cells in a medium without them. In addition, when a vector containing the LoxP is used, this can be achieved by introducing Cre recombinase into the cell concerned. Furthermore, when the transient expression vector and the introduction of RNA or protein are used, this may be achieved by bringing the cells out of contact with the vector or the like. The medium used in this step may be the same medium as described above.

The platelet production medium used in the step of culturing is not particularly limited and a known medium suitable for producing platelets from megakaryocytes or a medium equivalent to the medium may be used as appropriate. For example, a medium used for culturing animal cells may be prepared as a basal medium. Examples of the basal medium include IMDM medium, Medium 199, Eagle's Minimum Essential Medium (EMEM), αMEM, Doulbecco's modified Eagle's Medium (DMEM), Ham's F12 medium, RPMI 1640 medium, Fischer's medium, Neurobasal™ Medium (Life Technologies Japan Ltd.) and mixed media thereof.

The medium may contain serum or plasma or may be serum-free. As needed, the medium may also contain one or more substances, for example, albumin, insulin, transferrin, selenium, a fatty acid, trace elements, 2-mercaptoethanol, thiol glycerol, monothioglycerol (MTG), a lipid, an amino acid (for example, L-glutamine), ascorbic acid, heparin, a non-essential amino acid, a vitamin, a growth factor, a low molecular compound, an antibiotic, an antioxidant, pyruvic acid, a buffer, an inorganic salt, a cytokine, or the like. The cytokine is a protein that promotes hematopoietic differentiation and examples thereof include vascular endothelial growth factor (VEGF), thrombopoietin (TPO), various TPO-like agents, stem cell factors (SCFs), ITS (insulin-transferrin-celenite) supplements, and ADAM inhibitors. A preferred medium in the present invention is an IMDM medium containing serum, insulin, transferrin, serine, thiol glycerol, ascorbic acid, and TPO. The medium may further contain SCF and may further contain heparin. The concentrations thereof are also not particularly limited, but, for example, TPO may be at about 10 ng/mL to about 200 ng/mL or about 50 ng/mL to about 100 ng/mL; SCF may be at about 10 ng/mL to about 200 ng/mL or about 50 ng/mL; and heparin may be at about 10 U/mL to about 100 U/mL or about 25 U/mL. A phorbol ester (for example, phorbol-12-myristate-13-acetate, PMA) may be added.

In the method of production according to the present invention, the step of culturing megakaryocytes may be conducted under serum-free and/or feeder cell-free conditions. A preferable method involves culturing megakaryocytes produced according to the method of the present invention in a medium containing TPO. Conducting the step of producing platelets serum-free and feeder cells-free would hardly cause immunogenic problems unlikely when the obtained platelets are used clinically. Moreover, the production of platelets without using feeder cells would avoid the necessity of having feeder cells adhered and allow suspension culture in flasks and therefore suppress the production cost and be suitable for large-scale production. A conditioned medium may be used if feeder cells are not used. The conditioned medium is not particularly limited, and can be produced according to a method known to those skilled in the art or the like, and may be obtained, for example, by culturing feeder cells as appropriate and removing feeder cells from a culture with a filter.

The culture period can be determined as appropriate by monitoring the number of megakaryocytes and is, for example, about 2 days to 10 days or preferably 3 days to 7 days. It is desirable that the culture period be at least 3 days. Moreover, during the culture period, it is desirable that the culture be subcultured as appropriate.

A ROCK inhibitor and/or an inhibitor of actomyosin complex function are added to a platelet production medium. The ROCK inhibitor and the inhibitor of actomyosin complex function may be the same as those used in the method for producing multinucleated megakaryocytes as described above. Examples of the ROCK inhibitor include Y27632. Examples of the inhibitor of actomyosin complex functions include the myosin heavy chain II ATPase inhibitor Blebbistatin. The ROCK inhibitor may be added alone or the ROCK inhibitor and the inhibitor of actomyosin complex function may be added separately or added in a combination thereof.

The ROCK inhibitor and/or the inhibitor of actomyosin complex function are preferably added at 0.1 μM to 30 μM and, for example, 0.5 μM to 25 μM, 5 μM to 20 μM, or the like. The culture period after the addition of the ROCK inhibitor and/or the inhibitor of actomyosin complex function may be 1 to 15 days and may be 3 days, 5 days, 7 days, or the like. Addition of the ROCK inhibitor and/or the inhibitor of actomyosin complex function, can further increase the proportion of CD42b-positive platelets.

As described above, in the method for producing platelets according to the first aspect of one embodiment of the present invention, the culturing step of culturing megakaryocytes in a platelet production medium with the forced expression suppressed comprises a step of stirring the platelet production medium in a container using a stirring blade. And, the step of stirring preferably involves reciprocating the stirring blade such that one or more indicators selected from the following are satisfied for the purpose of minimum commercial production:

(a) turbulent energy of about 0.0005 $m^2/s^2$ to about 0.02 $m^2/s^2$;

(b) shearing stresses of about 0.2 Pa to about 6.0 Pa; and (c) a Kolmogorov scale of about 100 μm to about 600 μm.

The turbulent energy, shearing stresses, and Kolmogorov scale in the medium in the container to be stirred can be calculated by a simulation based on the basic equation of turbulence. For example, the calculation can be carried out using the thermal-fluid analysis software ANSYS® FLUENT®, but such software is not limited to a particular software. More specifically, the turbulent energy can change depending on when the stirring blade is configured to be reciprocated, the stroke of the reciprocation of the stirring blade, the speed of the reciprocation, the frequency of the reciprocation, and the like. When such an apparatus comprises a plurality of stirring blades, the number of stirring blades may be one factor that causes the change. The shearing stresses and the Kolmogorov scale may also change based on the change in similar factors.

In a certain embodiment, the indicators may be one or more selected from turbulent energy of about 0.0005 $m^2/s^2$ to about 0.015 $m^2/s^2$; shearing stresses of about 0.2 Pa to about 3.6 Pa; and a Kolmogorov scale of about 100 μm to about 600 μm. In another embodiment, the indicators may be one or more selected from turbulent energy of about 0.001 $m^2/s^2$ to about 0.016 $m^2/s^2$; shearing stresses of about 0.3 Pa to about 4.7 Pa; and a Kolmogorov scale of about 120 μm to about 440 μm; or one or more selected from turbulent energy of about 0.001 $m^2/s^2$ to about 0.015 $m^2/s^2$; shearing stresses of about 0.3 Pa to about 3.6 Pa; and a Kolmogorov scale of about 120 μm to about 440 μm. Moreover, in another embodiment, the indicators may be one or more selected from turbulent energy of about 0.002 $m^2/s^2$ to about 0.012 $m^2/s^2$; shearing stresses of about 0.5 Pa to about 3.6 Pa; and a Kolmogorov scale of about 160 μm to about 320 μm. These numerical ranges are for illustration purpose only and are not intended to limit the present invention. Moreover, these indicators may hereinafter be collectively referred to as indicators of turbulence.

An apparatus for producing platelets for carrying out the method of production according to the first aspect of one embodiment of the present invention will be described with reference to FIGS. 1 to 3.

Figure 2:
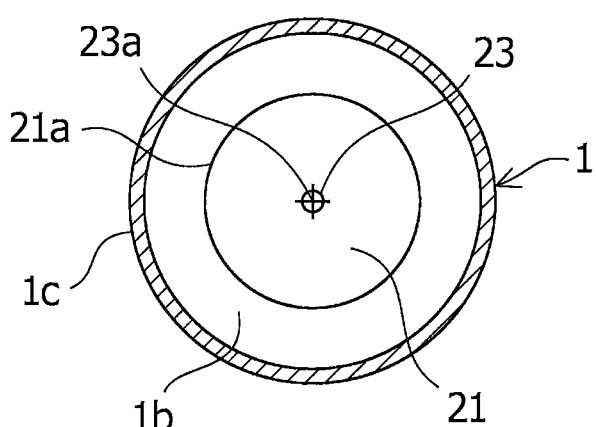
FIG. 2 is a transverse sectional view taken along the line A-A of FIG. 1.

As illustrated in FIGS. 1 and 2, the apparatus for producing platelets according to this aspect comprises a container 1 that holds a medium C in which megakaryocytes are suspended, and a stirring mechanism 2 having one stirring blade 21 that stirs the medium C in this container 1. The stirring mechanism 2 is configured to reciprocate the stirring blade 21. The directions of the reciprocation of the stirring blade 21 are indicated by the arrow R in FIG. 1. Furthermore, the stirring mechanism 2 controls the reciprocation of the stirring blade 21 such that any one of desired turbulent energy, shearing stresses, or Kolmogorov scale is produced in the medium C. Such a stirring mechanism 2 preferably controls the stroke of the reciprocation, the speed of the reciprocation (for example, the average speed of the reciprocation), the frequency of the reciprocation of the stirring blade 21, and the like. In particular, the reciprocation of the stirring blade 21 is preferably controlled in an unsteady pattern. The desired turbulent energy and shearing stresses can be calculated by a simulation as described above. The desired turbulent energy, shearing stresses, and Kolmogorov scale may be the same indicators as (a), (b), and (c) described above or within the numerical ranges described above for other embodiments. The apparatus for production produces platelets from megakaryocytes under such conditions.

Furthermore, the apparatus for production is preferably configured as follows. The container 1 in the apparatus for production is a hollow body and, in an example illustrated in FIGS. 1 and 2, the container 1 is formed in an approximately cylindrical shape. In the present invention, the container may be formed in a shape other than approximately cylindrical shapes, as long as it is a hollow body. Such a container 1 has a top wall (or top section) 1a and a bottom wall (or bottom section) 1b positioned opposite to each other on the vertical axis; and a circumference wall (or circumference section) 1c extending between the outer circumferential edges of the top wall 1a and the bottom wall 1b. Furthermore, the container 1 is preferably formed in an elongated shape extending in a substantially vertical direction.

In FIG. 1, the top wall 1a is a cover of the container 1 that is physically separated from the circumference wall 1c and the medium C can be transferred into the container 1 with the top wall 1a removed. In the present invention, a port for charging the container with a medium may be formed through the wall on the container and, in this case, the top wall may be integrally formed with the circumference wall in the container. Furthermore, the container in the present invention may be formed so as to open upward depending on the conditions for producing platelets and, in this case, an opening may be formed through the top wall or the container may have no top wall. The volume of the container 1 may be of any value as long as the container can produce platelets, but, for example, the volume of the container 1 is preferably about 300 mL or more, about 1 L or more, about 50 L or more, about 200 L or more, about 500 L or more, about 1,000 L or more, or about 2000 L or more, in terms of increasing the amount of platelets produced.

As illustrated in FIG. 1, the stirring blade 21 of the stirring mechanism 2 in the apparatus for production is placed along an intersection plane intersecting with the direction of the reciprocation at a predetermined intersection angle θ1. The intersection angle θ1 is about 90°. In other words, the stirring blade 21 is placed along an intersection plane approximately orthogonal to the direction of the reciprocation. The stirring blade 21 is formed in an approximately flat shape. An outer circumferential edge 21a of the stirring blade 21 is formed in an approximately circular shape in a view from a direction orthogonal to the intersection plane. As illustrated in FIGS. 1 and 2, the stirring blade 21 is placed with spaces before the top wall 1a, the bottom wall 1b, and the circumference wall 1c of the container 1. The stirring blade 21 may also be referred to as the "stirring vane". Moreover, another shape of the stirring blade 21 and the distance between the circumference wall 1c of the container 1 and the outer circumferential edge 21a of the stirring blade 21 may be determined according to the desired turbulent energy, the shearing stresses, or the Kolmogorov scale.

However, the stirring blade according to the present invention may have an intersection angle other than about 90° depending on the desired turbulent energy, shearing stresses, or Kolmogorov scale. Such an intersection angle may be in the range of about 0° to about 180°. Moreover, the stirring blade may be formed, depending on the desired turbulent energy, shearing stresses, or Kolmogorov scale, in a shape other than approximately flat shapes and, for example, the stirring blade may be formed in an approximate hemisphere shell shape, an approximate bowl shape, an approximate curved plate shape, an approximate waved plate shape, or the like. Furthermore, the outer circumferential edge of the stirring blade may be formed, depending on the desired turbulent energy, shearing stresses, or Kolmogorov scale, in a shape other than approximately circular shapes in a view from the direction orthogonal to the intersection plane, and, for example, the outer circumferential edge of the stirring blade may be formed, in a view from the direction orthogonal to the intersection plane, in an approximate semicircle shape, an approximate ellipse shape, an approximate semiellipse shape, an approximate fan shape, an approximate rectangle shape, an approximate polygon shape, an approximate star polygon shape. Moreover, the stirring blade may have at least 1 aperture penetrating in the direction of the reciprocation and the shape, the number, and the position of such apertures may be determined according to the desired turbulent energy, the shearing stresses, or the Kolmogorov scale.

Furthermore, as illustrated in FIG. 1, the stirring mechanism 2 has a driving source 22 for reciprocating the stirring blade 21 and a connection member 23 connecting the stirring blade 21 and the driving source 22. The driving source 22 is configured to reciprocate the stirring blade 21 by reciprocating the connection member 22. The driving source 22 may be configured to pivot, in addition to reciprocating, the stirring blade 21 and the connection member 23 around the axis 23a of the connection member 23. In this case, the stirring mechanism 2 may control, in addition to the control of the reciprocation of the stirring blade 21, the pivot speed and the pivot direction of the stirring blade 21 and, in particular, it is preferred that the reciprocation and pivot of the stirring blade 21 be controlled in an unsteady pattern.

Moreover, the connection member 23 is formed in an approximate shaft shape extending along the axis 23a. A longitudinal distal end 23b of the connection member 23 is attached to the stirring blade 21 and a longitudinal basal end 23c of the connection member 23 is reciprocatably held by the driving source 22. As illustrated in FIG. 2, the distal end 23b of the connection member 23 is attached to a position that approximately positions to the center of mass of the stirring blade 21. The distal end of the connection member may be attached to the position that deviates from the center of mass of the stirring blade, depending on the desired turbulent energy, shearing stresses, or Kolmogorov scale.

The stirring mechanism 2 is attached to the top wall 1a of the container 1. As to the specific structure for installing the stirring mechanism 2, an insertion aperture 1d penetrating in the direction of the reciprocation is formed through the top wall 1a of the container 1 and the stirring mechanism 2 is installed on the top wall 1a of the container 1, with the connection member 23 inserted through the insertion aperture 1d and the stirring blade 21 accommodated in the container 1. In the present invention, the stirring mechanism may be attached to the bottom wall or the circumference wall of the container, instead of the top wall of the container, by a specific installation structure of the stirrer as described above.

To enhance the sealability of the container 1, the apparatus for production may have a seal member 3 configured to close the gap between the circumferential edge the insertion aperture 1d of the container 1 and the connection member 23 of the stirring mechanism 2 while allowing the reciprocation of the connection member 23. For example, the seal member 3 may have a flexible structure that can adapt to the reciprocation of the connection member 23. Furthermore, the flexible structure may be a membrane structure made of a flexible material such as a rubber or the flexible structure may be a bellows structure made of a metal, Teflon (Registered Trademark), or the like. In the present invention, the seal member may be configured to hold the connection member slidable in the direction of the reciprocation.

The stirring blade 21 of the stirring mechanism 2 in such an apparatus for production reciprocates in the range of movement in the container 1. The range of movement is set in the container 1 or in the medium C such that the desired turbulent energy, shearing stresses, or Kolmogorov scale is obtained. In particular, the length of the range of movement in the direction of reciprocation, that is, the maximum stroke of the reciprocation of the stirring blade 21 and the position of the center of the range of movement in the direction of the reciprocation may be determined according to the length of the container 1 in the direction of the reciprocation, the distance from the bottom wall 1b of the container 1 to the surface c1 of the medium C, the volume of the container 1, the desired turbulent energy, shearing stresses, or Kolmogorov scale.

Furthermore, with reference to FIG. 3, an apparatus for production according to a modification of the first aspect will be described. The container 1 is illustrated using virtual lines in FIG. 3. According to a modification of the first aspect, the stirring mechanism 2 of the apparatus for production has two stirring blades 21, 24 placed with a space between the stirring blades in the direction of reciprocation. One of the two stirring blades 21, 24 (hereinafter, referred to as the "first stirring blade", as needed) 21 has a plurality of apertures 21b penetrating the blade in the direction of the reciprocation and the first stirring blade 21 is configured as same as the stirring blade 21 of the first aspect illustrated in FIGS. 1 and 2, except this point.

The other one of the two stirring blades 21, 24 (hereinafter, referred to as the "second stirring blade", as needed) 24 is configured as same as the stirring blade 21 of the first aspect, except the following. The second stirring blade 24 is attached to a longitudinal intermediate section 23d of the connection member 23. In FIG. 3, the intersection angle $\theta2$ of the second stirring blade 24 is an angle other than about 90°. However, in the present invention, the intersection angle of the second stirring blade may be an angle within the range between about 0° to about 180°, depending on the desired turbulent energy, shearing stresses, or Kolmogorov scale.

Furthermore, the first and second stirring blades 21, 24 have different shapes. The intersection angles $\theta1$, $\theta2$ of the first and second stirring blades 21, 24 are different from each other and the second stirring blade 24 is placed inclined to the first stirring blade 21. In FIG. 3, the outer circumferential edge 24a of the second stirring blade 24 is smaller than the outer circumferential edge 21a of the first stirring blade 21, as an example.

However, in the present invention, the first and second stirring blades may be configured in the same way as each other, except the positions at which they are attached, as long as the desired turbulent energy, shearing stresses, or Kolmogorov scale is provided. Moreover, in the present invention, the stirring mechanism may have three or more stirring blades placed with spaces between one another in the direction of the reciprocation depending on the length of the container in the direction of the reciprocation, the distance from the bottom wall of the container to the surface of the medium, the volume of the container, or the like, as long as the desired turbulent energy, shearing stresses, or Kolmogorov scale is provided.

Next, in the method for producing platelets according to the second aspect of one embodiment of the present invention, the step of culturing megakaryocytes with the forced expression suppressed in a platelet production medium comprises the step of stirring the platelet production medium in a container using a stirring blade pivotable around an approximately vertical axis and having at least part of the stirring blade in a bottom region of the container, and the step of stirring comprises pivoting the stirring blade, wherein a plurality of stationary members is placed around the stirring blade in the bottom region, such that turbulence in the medium is caused by the pivot of the stirring blade, in the medium.

Furthermore, apparatuses for producing platelets for carrying out the method of production according to the second aspect of one embodiment of the present invention will be described with reference to FIGS. 4 and 5.

Figures 3, 4:
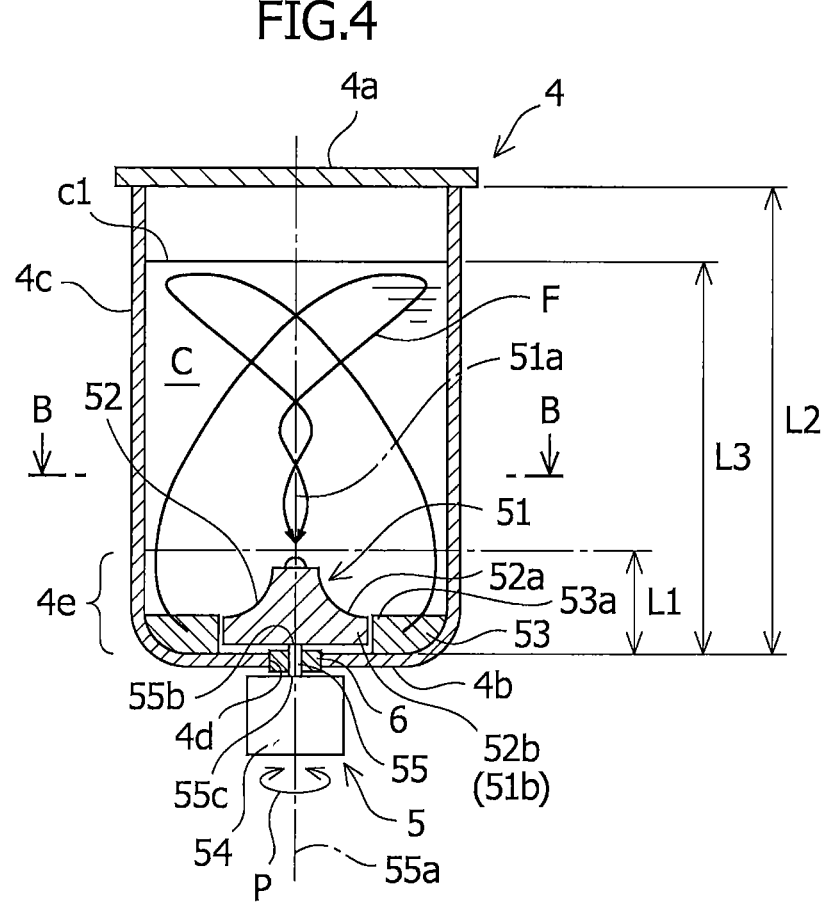
FIG. 3 is a perspective view schematically illustrating a container according to a modified aspect of the first aspect, first and second stirring blades, and a connection member.
FIG. 4 is a longitudinal sectional view schematically illustrating an apparatus for producing platelets according to the second aspect of one embodiment of the present inven-tion.
Figure 5:
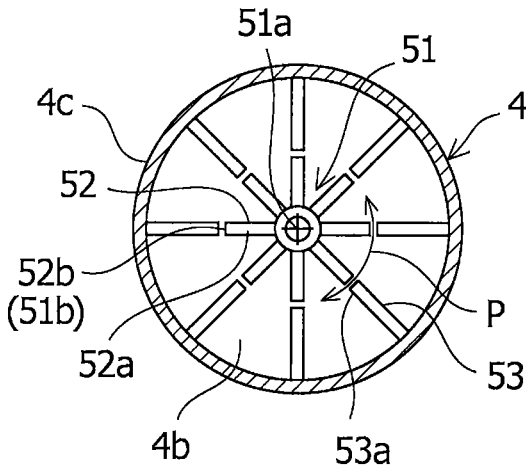
FIG. 5 is a transverse sectional view taken along the line B-B of FIG. 4.

As illustrated in FIGS. 4 and 5, an apparatus for producing platelets according to this aspect comprises a container 4 that holds a medium C in which megakaryocytes are suspended and a stirring mechanism 5 configured to stir the medium C such that turbulence in the medium C is caused in this container 4. The stirring mechanism 5 has a pivotable stirring blade 51. The directions of the pivot of the stirring blade 51 are indicated by the arrow P in FIG. 4. The stirring mechanism 5 is preferably configured such that the stirring blade 51 is pivotable in the both directions of the pivot. However, in the present invention, the stirring mechanism may be configured such that the stirring blade is pivotable in one of the directions of the pivot.

The stirring blade 51 is configured to be pivotal around an axis 51a extending approximately vertical from a bottom wall 4b of the container 4. The stirring blade 51 may have a plurality of vane portions 52 extending approximately radially from the axis 51a. A plurality of vane portions 52 may have spaces between one another in the directions of the pivot. In particular, the stirring blade 51 may be formed in an approximate impeller shape. Furthermore, the stirring mechanism 5 has a plurality of stationary members 53 placed around the stirring blade 51. Further details of the stirring blade 51 and the stationary members 53 are described below.

In such an apparatus for production, the stirring device 5 is configured to cause turbulence to stir the medium C by the interaction between the stirring blade 51 that pivots in the medium C and the stationary members 53 that stand still facing to this stirring blade 51. Furthermore, the stirring mechanism 5 controls the pivot of the stirring blade 51 such that the desired turbulent energy, shearing stresses, or Kolmogorov scale is produced in the medium C. In the stirring mechanism 5, the speed and the direction of the pivot of the stirring blade 51 may be controlled. In particular, the pivot of the stirring blade 51 is preferably controlled in an unsteady pattern. The desired turbulent energy, shearing stresses, or Kolmogorov scale can be calculated by a simulation similar to the first aspect except the conditions of the apparatus for production. The apparatus for production renews platelets from megakaryocytes such that the desired turbulent energy, shearing stresses, or Kolmogorov scale calculated is produced with the medium C stirred by the stirring device 5.

Furthermore, the apparatus for production is preferably configured as follows. As illustrated in FIG. 4, the container 4 of the apparatus for production has an insertion aperture 4*d* different from the insertion aperture 1*d* of the first aspect, as described below, but the container 4 is configured similarly to the container 1 according to the first aspect, except this point. The container 4 has a top wall (or top section) 4*a*, a bottom wall (or bottom section) 4*b*, and a circumference wall (or circumference section) 4*c*, respectively corresponding to the top wall 1*a*, the bottom wall 1*b*, and the circumference wall 1*c* according to the first aspect. An insertion aperture 4*d* that is used for the installation of the stirring device 5 is formed through the bottom wall 4*b* of the container 4. Moreover, the volume of the container 4 is also similar to the volume of the container 1 according to the first aspect.

The stirring blade 51 of the stirring mechanism 5 in the apparatus for production is placed relatively close to the bottom section 4*b* in the container 4. In particular, the stirring blade 51 is preferably placed entirely in a bottom region 4*e* of the container 4. In the present invention, the vertically upper part of the stirring blade may be located vertically higher than the bottom region, as long as the desired turbulent energy, shearing stresses, or Kolmogorov scale is produced.

The bottom region 4*e* may be defined as follows. The vertically bottom end of the bottom region 4*e* may approximately position to the vertical position of the bottom wall 4*b*. The vertically upper end of the bottom region 4*e* approximately positions to the position moved vertically upward by a predetermined length (that is, the vertical length of the bottom region 4*e*) L1 from the bottom wall 4*b*. The vertical length L1 of the bottom region 4*e* may be equal to or shorter than about half of the vertical length L2 of the container 4 or the vertical length L3 from the bottom wall 4*b* to the surface c1 of the medium C. For example, the vertical length L1 of the bottom region 4*e* may be about half, about ⅓, about ¼, about ⅕, or about 1/10 of the vertical length L2 of the container 4 or the vertical length L3 from the bottom wall 4*b* to the surface c1 of the medium C depending on the volume of the container 4, the desired turbulent energy, shearing stresses, or Kolmogorov scale.

Furthermore, an upper edge 52*a* of the vane portions 52 of the stirring blade 51 may become vertically lower as the position moves toward an outer circumference edge 51*b* of the stirring blade 51, that is, outer circumference edges 52*b* of the vane portions 52 from the axis 51*a* of the stirring blade 51. Moreover, other shapes and the number of the vane portions 52 of the stirring blade 51 and the distance between adjacent vane portions 52 may be determined depending on the desired turbulent energy, the shearing stresses, or the Kolmogorov scale.

Furthermore, a plurality of stationary members 53 is placed to be accommodated entirely in the bottom region 4*e* of the container 4. The internal circumference edges 53*a* of the stationary members 53 are apart from the outer circumference edge 51*b* of the stirring blade 51, that is, the outer circumference edges 52*b* of the vane portions 52. As illustrated in FIG. 4, the vertical upper ends of the internal circumference edges 53*a* of the stationary members 53 may be preferably located vertically higher than the vertical upper ends of the outer circumference edges 52*b* of the vane portions 52. Moreover, other shapes and the number of stationary members 53 and the distance between adjacent stationary members 53 may be determined depending on the desired turbulent energy, the shearing stresses, or the Kolmogorov scale.

Furthermore, the stirring mechanism 5 has a driving source 54 for pivoting the stirring blade 51 and a connection member 55 connecting the stirring blade 51 and the driving source 54. The driving source 54 is configured to pivot the stirring blade 51 by pivoting the connection member 55.

The connection member 55 is formed in an approximate shaft shape extending along the axis 55*a*. The axis 55*a* of the connection member 55 positions to the axis 51*a* of the stirring blade 51. The longitudinally distal end 55*b* of the connection member 55 is attached to the stirring blade 51 and the longitudinally basal end 55*c* of the connection member 55 is pivotably held in the driving source 54.

The stirring mechanism 5 is attached to the bottom wall 4*b* of the container 4. As to the specific installation structure of the stirring mechanism 5, the insertion aperture 4*d* formed through the bottom wall 4*b* of the container 4 vertically penetrates the bottom wall 4*b* as described above. The stirring mechanism 5 is installed on the bottom wall 4*b* of the container 4 with the connection member 55 inserted through the insertion aperture 4*d* and the stirring blade 51 accommodated in the container 4.

The apparatus for production may have a seal member 6 configured to close the gap between the circumferential edge the insertion aperture 4*d* of the container 4 and the connection member 55 of the stirring mechanism 5 while allowing the pivot of the connection member 55.

For example, the seal member 6 may be a sealing bearing or the like.

In the apparatus for production according to the second aspect, such circulating flows as illustrated by the arrow F in FIG. 4 may be caused in the medium C in the container 4. As to the circulating flows, specifically, the interaction between the pivoting stirring blade 51 of the stirring mechanism 5 and the stationary members 53 that stand still causes a flow from the stationary members 53 to run upward along the circumference wall 4*c* of the container 4, the upward flow runs so as to swirl up to near the surface c1 of the medium C, then the flow that has reached the vicinity of the surface c1 of the medium C runs downward, the downward flow runs so as to swirl toward the axis 51*a* of the stirring blade 51 and then reaches the stirring blade 51, and again the interaction between the pivoting stirring blade 51 of the stirring mechanism 5 and the stationary members 53 that stand still causes a flow from the stationary members 53 to run upward along the circumference wall 4*c* of the container 4. By such circulating flows, it is possible to promote the production of platelets from megakaryocytes and increase the amount of platelets produced.

Further preferred conditions for the method of production and apparatuses of production according to the first and second aspects as described above will be described below. Hereinafter, the invention will be described without using the reference numerals in FIGS. 1 to 5.

The step of culturing megakaryocytes under conditions in which the predetermined turbulent energy, shearing stresses, or Kolmogorov scale according to the first aspect is provided or the step of culturing under conditions in which the stirring blade is pivoted such that turbulence is caused in the medium according to the second aspect may be conducted from the start of the step of culturing with the forced expression suppressed, that is, from the time of start of culturing in a platelet production medium or may be conducted 1 to 3 days before the step of collecting platelets. Moreover, such conditions may be provided intermittently during the culture period, but are preferably provided continuously from the start of the step of culturing with the forced expression suppressed. Furthermore, the predetermined preferred turbulent energy, shearing stresses, or Kolmogorov scale may be maintained almost constant during the culture period or variably adjusted.

By culturing megakaryocytes in a platelet production medium under conditions in which the predetermined turbulent energy or shearing stresses according to the first aspect or by culturing megakaryocytes in a platelet production medium under conditions in which the stirring blade is pivoted such that turbulence is caused in the medium according to the second aspect, the release of platelet production promoting factors including macrophage migration inhibitory factor (MIF), nardilysin (also referred to as N-arginine dibasic convertase; NRDc, NRD1 protein), insulin-like growth factor binding protein 2 (IGFBP2), 1 thrombospondin 1 (TSP-1), plasminogen activator inhibitor (PAI-1), and CCL5 (RANTES: regulated on activation, normal T cell expressed and secreted)) from megakaryocytes can be promoted to increase the amounts of MIF, NRDc, IGFBP2, TSP-1, PAI-1, and CCL5 in the medium. By increasing the amounts of these platelet production promoting factors in the medium and culturing with megakaryocytes provided with such physical stimulation that the turbulent energy, shearing stresses, or Kolmogorov scale will be in the preferred indicator range described above in the presence of such factors, the amount of platelets produced from a megakaryocyte can be increased.

Optionally, the culturing step involving pivoting the stirring blade so as to provide the predetermined turbulent energy, shearing stresses, or Kolmogorov scale according to the first aspect or to cause turbulence in the medium according to the second aspect may comprise adding platelet production promoting factors including MIF, NRDc, and IGFBP2 exogenously to the megakaryocytes. The platelet production promoting factors added exogenously necessarily include the three factors MIF, NRDc, and IGFBP2, but are preferably the six factors including, in addition to the three factors, TSP-1, PAI-1, and CCL5. This is because it becomes possible to further promote the production of platelets from megakaryocytes with the six factors.

These platelet production promoting factors added exogenously may be obtained by any method, but are preferably genetic recombinants obtained by a genetic recombination technique.

The gene recombinants may be those that are commercially available or produced by one skilled in the art as appropriate according to known genetic information. For example, MIF, IGFBP2, TSP-1, PAI-1, and CCL5 are widely commercially available and commercially available proteins may be used. The isolation and purification of NRDc has been reported in J. Biol. Chem., 269, 2056, 1994 and the genetic sequence thereof has been reported in Proc. Natl. Acad. Sci. USA, 91, 6078, 1994. Accordingly, it can be produced by a method known in the field based on the information disclosed in these documents or other known documents. The concentrations of the platelet production promoting factors to be added are not particularly limited, but, for example, NRDc, IGFBP2, TSP-1, PAI-1, and CCL5 are preferably added to be about 10 to 500 ng/mL and further preferably to be about 50 to 100 ng/mL. MIF is preferably added to be about 1 to 500 ng/mL and further preferably to be about 10 to 100 ng/mL. However, the amounts of addition are not particularly limited, and can be determined by one skilled in the art can as appropriate.

The step of adding platelet production promoting factors exogenously may be conducted at the start of culturing in a platelet production medium with the forced expression suppressed, but is preferably conducted 1 to 3 days before the step of collecting platelets. This is because the platelet production promoting factors added exogenously may be deteriorated before the step of collecting platelets. Moreover, the platelet production promoting factors may also be added several times at time intervals, not in a single dose. In either case, the platelet production promoting factors are preferably added such that the platelet production promoting factors are present in the medium at the time of the release of platelets from megakaryocytes.

Platelets are collected from the medium by a usual method such as FACS in the step of collecting platelets to be conducted next. The "platelets" are one of the cellular components in the blood and characterized by being CD41a positive and CD42b positive. The platelets play important roles in thrombogenesis and hemostasis and are also involved in tissue regeneration after damaging and the pathophysiology of inflammation. The activation of platelets by hemorrhage or the like leads to the expression of receptors of cell adhesion factors such as Integrin $\alpha IIB\beta 3$ (glycoprotein IIb/IIIa; a complex of CD41a and CD61) on the membrane. As a result, platelets agglutinate and a thrombus is formed and hemostasis progresses by fibrin clotting by blood coagulation factors released from platelets.

The function of platelets may be measured and evaluated by a known method. For example, the amount of activated platelets can be measured using an antibody against PAC-1 that specifically binds to Integrin $\alpha IIB\beta 3$ on the membrane of the activated platelets. Moreover, the activated platelet marker CD62P (P-selectin) may similarly be detected with an antibody to measure the amount of activated platelets. For example, this can be carried out by the gating using an antibody against an activation-independent platelet marker CD61 or CD41 by flow cytometry and subsequent detection of the binding of an anti-PAC-1 antibody or an anti-CD62P antibody. These steps may be conducted in the presence of adenosine diphosphate (ADP).

Moreover, the evaluation of the function of platelets may be conducted based on the binding with fibrinogen in the presence of ADP. The binding of platelets with fibrinogen causes the activation of integrin required early in thrombogenesis.

Figure 6:
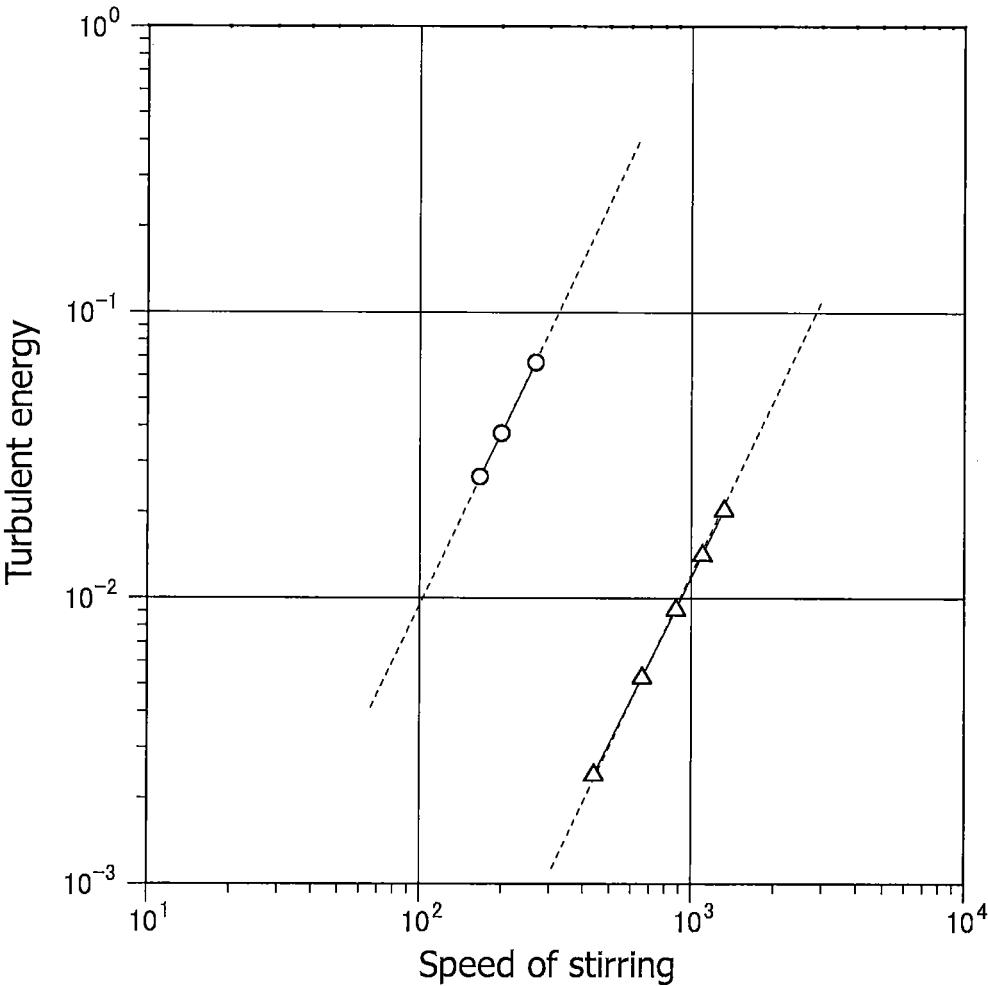
FIG. 6 is a graph illustrating the relationship between the stirring speed and the turbulent energy when a reciprocating unsteady bioreactor is used and when a one-way rotary bioreactor is used.

Furthermore, the evaluation of the function of platelets may be conducted by a method for visualizing and observing the capacity of thrombogenesis in vivo as shown in FIG. 6 in International Publication No. WO 2011/034073.

The platelets obtained by the method of production according to the present invention can be administered to patients as a formulation. For the administration of the platelets obtained by the method according to the present invention, the platelets may be stored and formulated, for example, in human plasma, an infusion, physiological saline containing citric acid, a liquid containing acetate Ringer solution with glucose as a main ingredient, PAS (platelet additive solution) (Gulliksson, H., et al., Transfusion, 32: 435-440, (1992)), or the like. The storage period is about 3 to 7 days, and preferably 4 days. The storage is preferably conducted at room temperature (about 20 to 24° C.) with stirring by shaking.

In addition, in the method of production of the platelet according to the present embodiment, about the general culture condition except a predetermined turbulent energy condition, shearing stresses condition, a Kolmogorov scale condition and the stirring condition, US2012/0238023A1 (International Publication No. WO 2011/034073), US2014/0127815A1 (International Publication No. WO 2012/157586), and US2016/0002599A1 (International Publication No. WO 2014/123242) disclosing nonlimiting examples of methods for producing megakaryocytes and methods for producing platelets are herein incorporated by reference.

[Methods for Determining Operating Conditions of Apparatus for Producing Platelets]

According to another embodiment, the present invention also relates to a method for determining operating conditions of an apparatus for producing platelets and particularly relates to a method for determining operating conditions of an apparatus for producing platelets comprising a reciprocatable stirring blade such as that according to the first aspect of the embodiment or a method for determining operating conditions of an apparatus for producing platelets comprising a pivotable stirring blade such as that according to the second aspect of the embodiment. The methods according to this embodiment comprise calculating the correlation between one or more indicators selected from turbulent energy, shearing stresses, and a Kolmogorov scale and the number of platelets produced in an apparatus for producing platelets, comprising a reciprocatable or pivotable stirring blade and determining operating conditions that provide the indicators with which the number of platelets produced is in a predetermined range.

The methods for determining operating conditions according to this embodiment can be conducted for any apparatus comprising a reciprocatable or pivotable stirring blade. The step of calculating the correlation involves adjusting the conditions of items to be stirred, such as the medium and the number of megakaryocytes to be seeded, to certain conditions in a particular apparatus and changing a turbulent energy condition and counting the number of platelets produced obtained with the condition. In conditions in which a plurality of values for example, three or more values, of one or more indicators, for example, turbulent energy, are provided, the correlation with the turbulent energy and the number of platelets produced is obtained by obtaining the respective numbers of platelets produced in the conditions. Alternatively, the correlation may also be obtained similarly using the shearing stresses or the Kolmogorov scale, instead of the turbulent energy, as a value to be the indicator.

In the step of determining the operating conditions, the range of the turbulent energy, shearing stresses, or Kolmogorov scale for providing a preferred number of platelets produced is determined based on the correlation obtained in the step. The preferred range can be determined as appropriate based on the number of platelets produced required by those skilled in the art, but the preferred range may be defined as conditions of the turbulent energy, shearing stresses, or Kolmogorov scale that provide the number of platelets produced that is, for example, 50% or more, 60% or more, 70% or more, 80% or more, 85% or more, 90% or more, or 95% or more of the maximum number of platelets produced in the measurement range. The operating conditions that provide the turbulent energy, shearing stresses, or Kolmogorov scale are determined. Examples of the operating conditions of the apparatus for producing platelets comprising a reciprocatable stirring blade include, but are not limited to, the speed of the reciprocation (for example, the average speed of the reciprocation) of the stirring blade, the period of the reciprocation, and the stroke of the reciprocation. Specifically, to define the preferred range as conditions of turbulent energy, shearing stresses, or Kolmogorov scale, the average speed of reciprocation of the stirring blade may be adjusted to, but is not limited to, the range of 50 mm/s to 500 mm/s. Examples of the operating conditions of the apparatus for producing platelets comprising a pivotable stirring blade include, but are not limited to, the speed and the direction of pivot of the stirring blade.

The methods according to this embodiment are based on the discovery by the present inventors that the efficiency of production of platelets has a strong correlation with the turbulent energy or shearing stresses in the container of the apparatus for production and this correlation is substantially constant independent from the scale of the container. The methods according to this embodiment are advantageous in that appropriate operating conditions that are highly efficient in the production of platelets can be determined easily when an apparatus in a different mode is newly introduced or when an apparatus is scaled up.

EXAMPLES

The present invention will be described in more details referring to Examples. However, the following Examples are not intended to limit the present invention.

[Preparation of Multinucleated Megakaryocytes]

The cell-culturing of immortalized megakaryocyte progenitor cell line Cl-7 produced by introducing c-MYC, BMI1, and BCL-XL simultaneously into hematopoietic stem cells derived from iPS cells (TKDN SeV2: human fetus skin fibroblast-derived iPS cells established by using Sendai virus, 585A1, 585B1, 606A1, 648B1, and 692D2: human peripheral blood mononuclear cell-derived iPS cells established by using an episomal vector described in Okita K, et al, Stem Cells 31, 458-66, 2012) established by the method described in Nakamura et al, Cell Stem Cell. 2014 Apr. 3; 14(4): 535-48 and International Publication No. WO 2014/123242 was conducted as a starting material based on the method described on page 12 in Nakamura et al., Cell Culture. The Gene ON medium used at this time was the ESC differentiation medium described in Takayama et al., Blood. 2008 Jun. 1; 111 (11): 5298-306 supplemented with SCF and TPO at the concentrations described before and 5 μg/ml of Doxycycline. The cells used in the following experiments were prepared in this way.

imMKCL was cultured for 6 days using a platelet production medium after Gene (c-MYC, BMI1, BCL-XL) Off. The platelet production medium (Gene Off medium) was the IMDM medium supplemented with 1×ITS, 2 mM L-Glu, 50 μg/mL ascorbic acid, 450 μM MTG, 5% human plasma, 10 U/mL Heparin, 50 ng/ml human stem cell factor (SCF), 200 ng/mL TA-316, 0.5 μM GNF-351, 0.5 μM ROCK (Rho associated protein kinase) inhibitor Y-39983, 15 μM ADAM 17 inhibitor KP457 (Hirata et al., Stem Cell Translational Medicine, in press). The culturing was conducted with the reciprocating unsteady bioreactor (VerMES VMF3000, Satake Chemical Equipment Mfg., Ltd.), rotary shaken flasks, and culture dishes.

[Comparison of Reciprocating Unsteady Bioreactor and One-Way Rotary Bioreactor]

The relationships of the turbulent energy and the stirring speed in a reciprocating unsteady bioreactor and a one-way rotary bioreactor were compared. The reciprocating unsteady bioreactor used was VerMES VMF3000 (Satake Chemical Equipment Mfg., Ltd.). The rotary bioreactor used was a non-reciprocating reactor having a single stirring blade provided in the bottom section and the stirring blade pivoting only in one direction. The stirring speed in the reciprocating unsteady bioreactor refers to the average travelling speed and the average travelling speed is defined as the speed of the stirring blade from the bottom dead center to the top dead center (or vice versa) in the up and down movements. The stirring speed in the one-way rotary bioreactor refers to the distal circumference speed of the stirring blade: the ratio $\pi$ of the circumference of a circle to its diameter×rotational frequency N (rps)×blade diameter (mm). The turbulent energy was calculated using the thermal-fluid analysis software ANSYS® FLUENT®.

The relationships of the stirring speed and the turbulent energy in a reciprocating unsteady bioreactor and a one-way rotary bioreactor are shown in FIG. 6. In the graph, the relationship of the stirring speed and the turbulent energy in the reciprocating unsteady bioreactor is represented by open circles and the relationship of the stirring speed and the turbulent energy in the rotary bioreactor that has been used conventionally is represented by triangles. The reciprocating unsteady bioreactor is characterized in that the turbulent energy of the stirring blade at the average travelling speed is very low in comparison with the rotary bioreactor. The characteristic that high turbulent energy is obtained without providing an excessive driving speed is useful for the development of a reactor for the industrialization that requires scaling up. The rotary bioreactor is considered to be difficult in controlling the shear effect because the operation at higher rotational frequencies is demanded.

[Relation Between Turbulent Energy or Shearing Stresses and Number of Platelets Produced]

Figure 7:
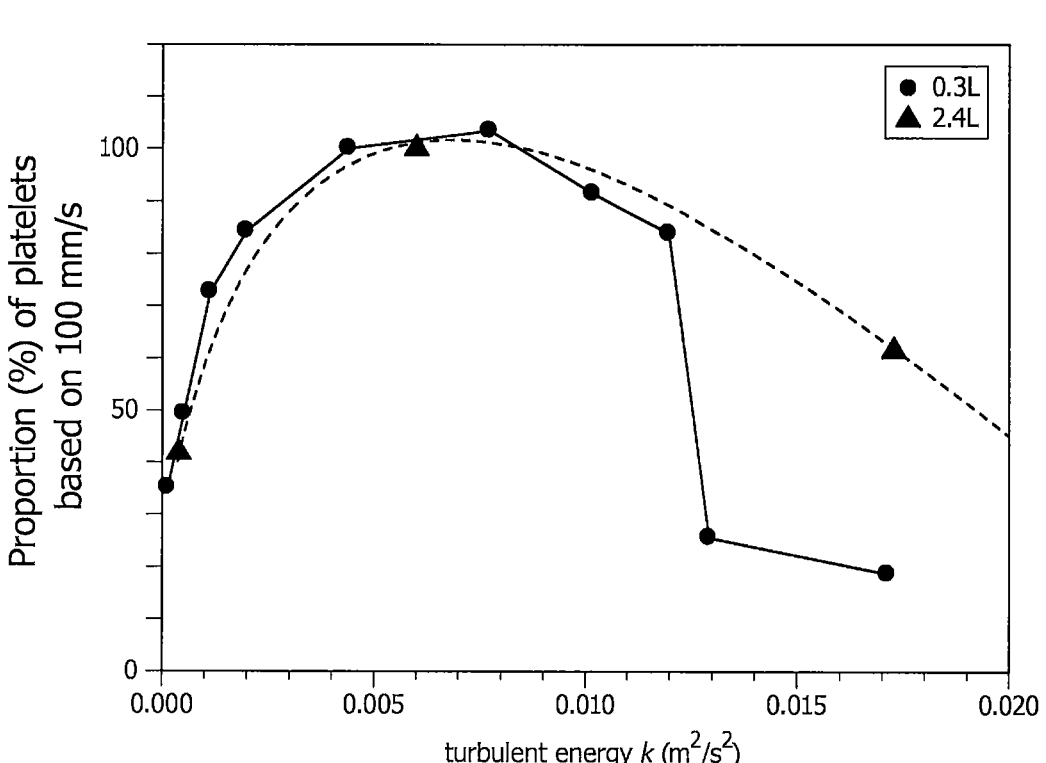
FIG. 7 is a graph illustrating the relation between the turbulent energy and the number of platelets produced (the ratio (%) to the number of platelets produced at a stirring speed of 100 mm/s) when a reciprocating unsteady biore-actor is used.
Figure 8:
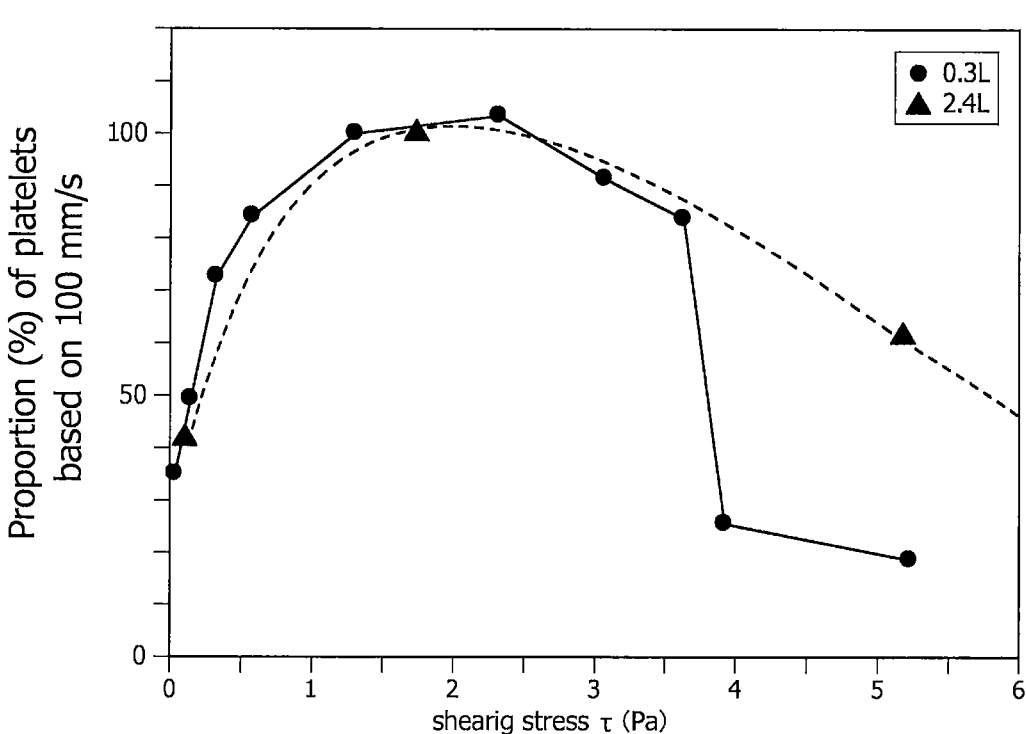
FIG. 8 is a graph illustrating the relationship between shearing stresses and the number of platelets produced (the ratio (%) to the number of platelets produced at a stirring speed of 100 mm/s) when a reciprocating unsteady biore-actor is used.
Figure 9:
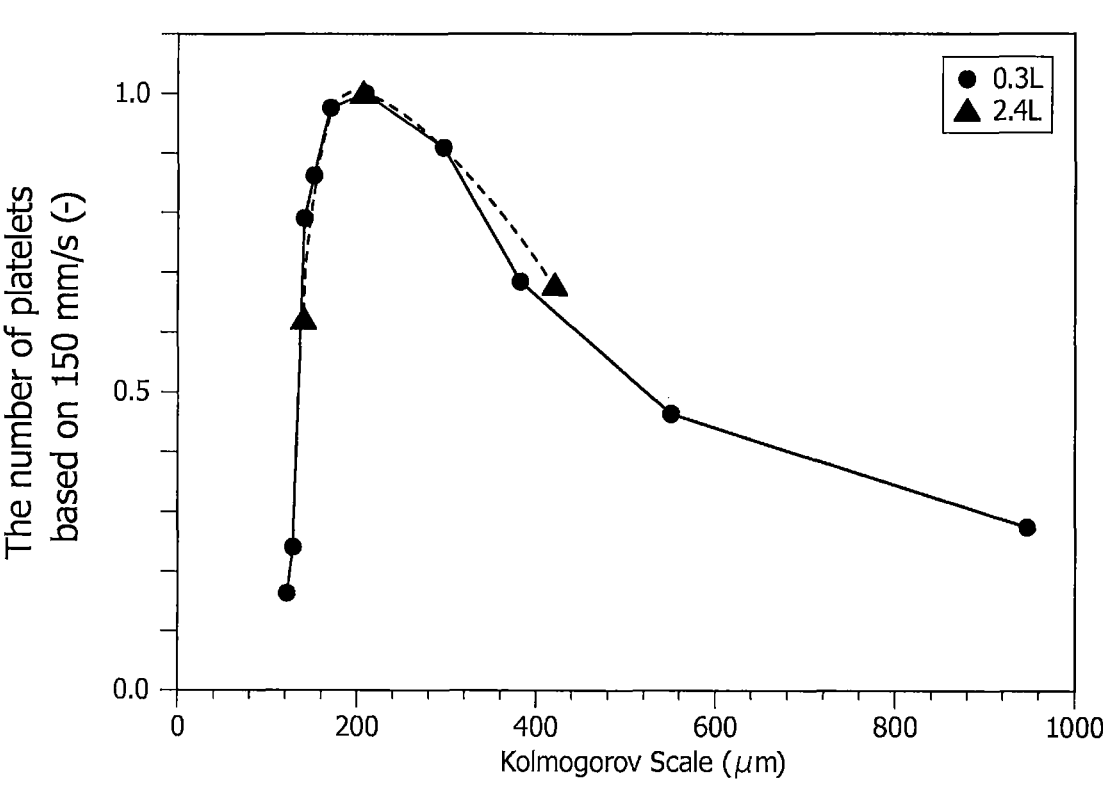
FIG. 9 is a graph illustrating the relation between the Kolmogorov scale and the number of platelets produced (the ratio (%) to the number of platelets produced at a stirring speed of 150 mm/s) when a reciprocating unsteady biore-actor is used.

Next, the relationships of turbulent energy and shearing stresses with the proportion of the numbers of platelets produced (%) based on that at 100 mm/s were examined using reciprocating unsteady bioreactors VerMES having different capacities. Moreover, the relationship of the Kolmogorov scale and the proportion of the number of platelets produced based on that at 150 mm/s was examined. The proportion (%) of platelets based on that at 100 mm/s is a proportion (%) of the number of platelets (platelets/mL) in each condition in the medium after the culturing step for 6 days while the number of platelets when the stirring speed (the average travelling speed) is 100 mm/s being 100%. The bioreactor used was 0.3 L VerMES and 2.4 L VerMES. The values of the turbulent energy were calculated using the thermal-fluid analysis software ANSYS® FLUENT® in the same manner as the above. Moreover, the shearing stresses and the Kolmogorov scale were calculated using the software. The results are shown in FIGS. 7 to 9. From these results, it was suggested that the efficiency of production of platelets can be maintained by causing turbulent energy or shearing stresses in a predetermined range even when using bioreactors VerMES having different capacities.

Figure 10:
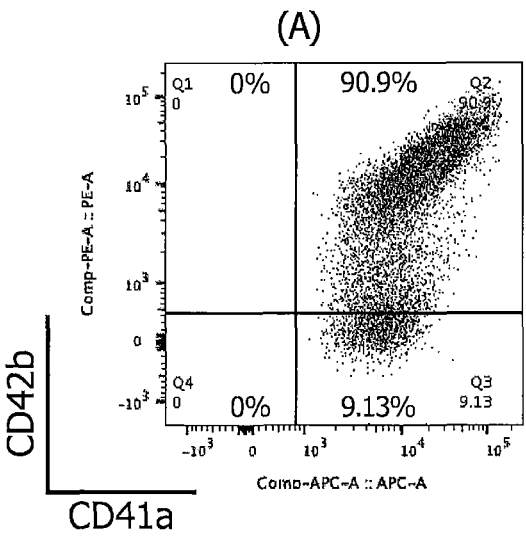
FIG. 10 illustrates the results of measurement of the physiological activity of platelets when a 50 L reciprocating unsteady bioreactor is used.
Figure 10:
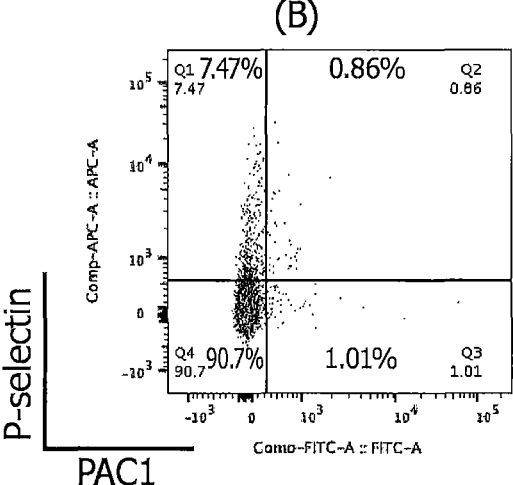
Figure 10:
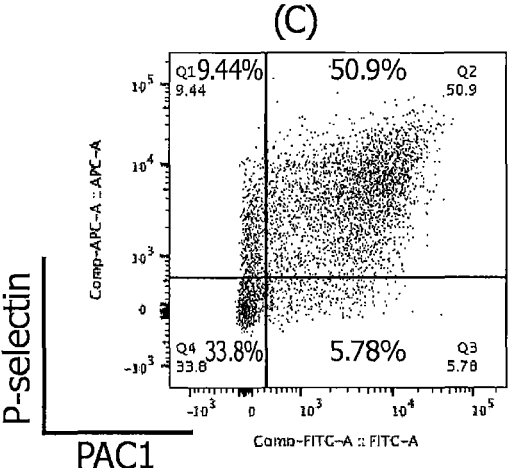
Figure 11:
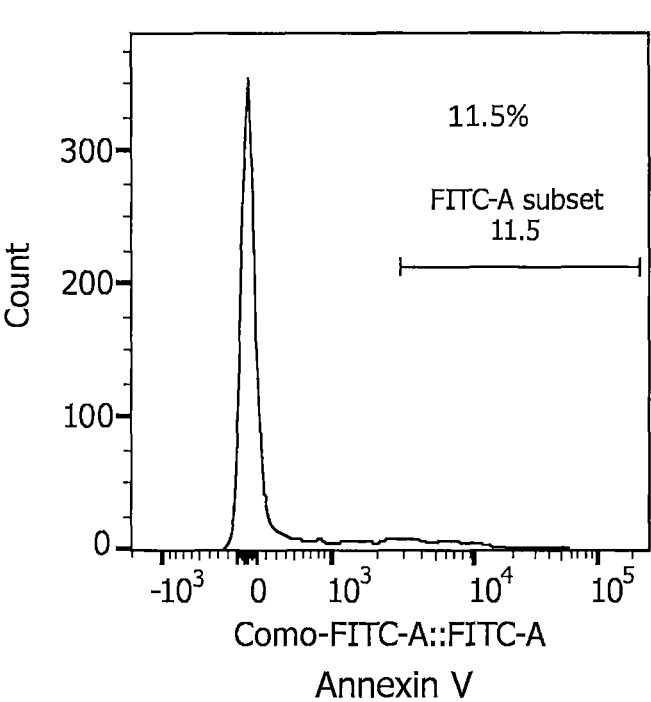
FIG. 11 illustrates the results of measurement of the physiological activity of platelets when a 50 L reciprocating unsteady bioreactor is used.
Figure 11:
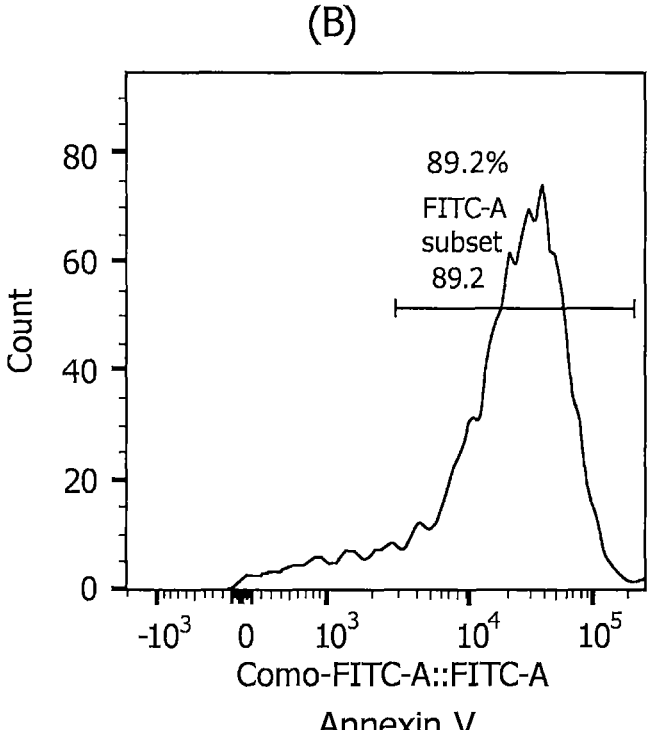

Next, the physiological activity (at a stirring speed of 400 mm/s) of platelets was measured using a 50 L reciprocating unsteady bioreactor VerMES. The results are illustrated in FIG. 10 and FIG. 11. Referring to FIG. 10(A), the proportion of normal platelets that are CD41a-positive and CD42b-positive was 0.9%. FIG. 10(B) illustrates the proportion of P-selectin-positive platelets when platelets are not stimulated, and FIG. 10(C) illustrates the proportion of P-selectin-positive platelets when platelets are stimulated with ADP+ TRAP6. When platelets are stimulated with ADP+TRAP6, PAC-1-positive and P-selectin-positive platelets are increased by stimulation in comparison with no stimulation, and it was confirmed that the platelets maintained high physiological activity.

FIG. 11(A) illustrates the proportion of annexin V-positive platelets when platelets are not stimulated and FIG. 11(B) illustrates the proportion of annexin V-positive platelets when platelets are stimulated with Ionomycin. When platelets are stimulated with Ionomycin. When the number of annexin V-positive particles was counted as platelets that were not normal, the proportion of annexin V positive with no stimulation was as low as 11.5% and the proportion of annexin V positive became 89.2% with Ionomycin stimulation, with the high physiological activity maintained.

[Relationships of Turbulent Energy or Shearing Stresses with Thrombopoietin]

The amount of NRDc secreted in the medium after culturing for 6 days under the above-described culturing conditions in which different indicators of turbulence were provided was quantified by ELISA. The result is shown in Table 1. In the table, Sample 1 was a sample when a reciprocating unsteady bioreactor was used under stirring conditions in which the turbulent energy was about 0.00013 $m^2/s^2$, the shearing stresses was about 0.03 Pa, and the Kolmogorov scale was 948 μm. Sample 2 was a sample when a reciprocating unsteady bioreactor was used under stirring conditions in which the turbulent energy was about 0.002 $m^2/s^2$, the shearing stresses was about 0.64 Pa, and the Kolmogorov scale was about 296 μm. Sample 3 was a sample when a reciprocating unsteady bioreactor was used under stirring conditions in which the turbulent energy was about 0.0047 $m^2/s^2$, the shearing stresses was about 1.42 Pa, and the Kolmogorov scale was about 210 μm. Sample 4 was a sample when a reciprocating unsteady bioreactor was used under stirring conditions in which the turbulent energy was about 0.0174 $m^2/s^2$, the shearing stresses was about 4.25 Pa, and the Kolmogorov scale was about 122 μm. The numerical values in the table are expressed as the concentration (pg/ mL) of NRDc.

TABLE 1

|  | Sample 1 | Sample 2 | Sample 3 | Sample 4 |
| --- | --- | --- | --- | --- |
| NRDc concentration | 2,277 | 4,567 | 12,770 | 5,621 |

Similarly, the concentrations of MIF, IGFBP2, TSP-1, PAI-1, and CCL5 in the medium after culturing under different culturing conditions were measured. The quantification was conducted using Human XL Cytokine ArrayKit (R & D, #ARY022). The results are shown in Table 2. In the table, Samples 1 to 4 were under similar conditions as in Table 1. In culturing in culture dishes, the turbulent energy, the shearing stresses, and the Kolmogorov scale were approximately 0. In culturing in flasks, the turbulent energy was about 0.000025 $m^2/s^2$, the shearing stresses was about 0.016 Pa, and the Kolmogorov scale was about 31 μm. The numerical values in the table are expressed as the proportion of the concentration in the sample while the concentration of the factor in culturing in culture dishes was 1.00.

TABLE 2

|  | Dish | Flask | Sample1 | Sample2 | Sample3 | Sample4 |
| --- | --- | --- | --- | --- | --- | --- |
| IGFBP-2 | 1.00 | 1.07 | 1.15 | 1.23 | 1.38 | 1.23 |
| MIF | 1.00 | 1.23 | 1.42 | 1.78 | 1.99 | 1.81 |
| CCL5 | 1.00 | 1.05 | 1.16 | 1.12 | 1.17 | 0.95 |
| PAI-1 | 1.00 | 1.06 | 1.26 | 1.23 | 1.22 | 0.73 |
| TSP-1 | 1.00 | 1.01 | 1.24 | 1.18 | 1.12 | 1.04 |

From these experiments, it was confirmed that the amount of thrombopoietin secreted was increased under stirring conditions in which the turbulent energy, the shearing stresses, and the Kolmogorov scale were in the predetermined ranges.

REFERENCE SIGNS LIST

1 container, 2 stirring mechanisms, 21 stirring blade (first stirring blade), 24 second stirring blade, 4 container, 4*b* bottom wall (bottom section), 4e bottom region, 5 stirring mechanism, 51 stirring blade, 51a axis, 53 stationary members, C medium.

The invention claimed is:

1. A method for producing platelets within an apparatus, the apparatus comprising a container that contains a platelet production medium in which megakaryocytes are suspended, and a stirring mechanism comprising a shaft and at least two flat-shaped stirring blades attached spaced apart and perpendicular to the shaft, the method comprising culturing the megakaryocytes in the platelet production medium, wherein the culturing comprises stirring the platelet production medium by driving the stirring mechanism to expose the megakaryocytes to shearing stress and turbulence, and wherein the stirring comprises reciprocating the at least two flat-shaped stirring blades in an unsteady pattern by varying a stroke, a speed, or a frequency of reciprocation of the stirring mechanism such that one or more indicators selected from the following are satisfied:

(a) turbulent energy of about 0.002 m$^2$/s$^2$ to about 0.012 m$^2$/s$^2$;

(b) shearing stresses of about 0.5 Pa to about 3.6 Pa; and (c) a Kolmogorov scale of about 160 μm to about 320 μm, and wherein an average speed of reciprocation of the at least two stirring blades is in the range of 50 mm/s to 500 mm/s.

2. The method according to claim 1, comprising, prior to the step of culturing the megakaryocytes, a step of forcibly expressing an oncogene, a polycomb gene, and an apoptosis repressor gene in cells less differentiated than megakaryocytes to obtain immortalized megakaryocytes.

3. The method according to claim 1, comprising a step of collecting platelets obtained in the step of culturing megakaryocytes.

4. The method according to claim 1, wherein the step of stirring comprises a step of adding platelet production promoting factors including Macrophage migration inhibitory factor (MIF), N-arginine dibasic convertase (NRDc), and Insulin-like growth factor binding protein 2 (IGFBP2) exogenously.

5. The method according to claim 4, wherein the exogenously added platelet production promoting factors further comprise Thrombospondin-1 (TSP-1), Plasminogen activator inhibitor-1 (PAI-1), and C-C motif chemokine ligand 5 (CCL5).

* * * * *